United States Patent [19]

Skulnick et al.

[11] Patent Number: 4,495,349
[45] Date of Patent: Jan. 22, 1985

[54] 6-ARYLURACILS

[75] Inventors: Harvey I. Skulnick; Herman W. Smith; Robert J. Smith; Wendell Wierenga, all of Kalamazoo, Mich.

[73] Assignee: The Upjohn Company, Kalamazoo, Mich.

[21] Appl. No.: 512,497

[22] Filed: Jul. 11, 1983

[51] Int. Cl.$^3$ ................ C07D 265/10; A61K 31/535
[52] U.S. Cl. ........................................ 544/97; 544/96; 514/825
[58] Field of Search .............................. 544/88, 96, 97

[56] References Cited

U.S. PATENT DOCUMENTS 4,171,429 10/1979 Watanabe et al. .................. 424/251

FOREIGN PATENT DOCUMENTS 882315 9/1980 Belgium .............................. 424/251
2142317 3/1973 Fed. Rep. of Germany ...... 424/251
57-03551 2/1982 Japan .................................. 424/251

OTHER PUBLICATIONS

Johnson et al., "J. Am. Chem. Soc.", vol. 37, pp. 378–383 (1915).
Gershon et al., "J. Med. Chem.", vol. 6, pp. 87–89 (Jan., 1963).
Lacey, "J. Chem. Soc.", pp. 839–844 (1954).
Moszew et al., "New Type of Addition of Aromatic Isocyanates to Benzoylacetamide, 1,6-Diaryl Derivatives of Uracil," Zesz. Nauk. Univ. Jagiellon, Pr. Chem. 1969, No. 14, pp. 31–45, C.A. 72:12242e.
Hannon et al., Tetrahedron Letters, 21, 1105 (1980).
Clark et al., "Heterocyclic Studies, Part XIX, Some 6-(Substituted phenyl)-uracil and -thiouracil Derivatives, J. Chem. Soc. (C)., pp. 1945–1948 (1971).
Clark et al., "Heterocyclic Studies, Part XXVII, Mass Spectra of 6-(meta- and para- Substituted -phenyl)-uracil and -thiouracil Derivatives", J. Chem. Soc. Perkin II, pp. 233–237 (1972).
Senda et al., "Pyrimidine Derivatives and Related Compounds, 15, Synthesis and Analgetic and Antiinflammatory Activities of 1,3-Substituted 5-Amino-6-Methyluracil Derivatives", J. Med. Chem., vol. 15, No. 5, pp. 471–476 (1972).
Derwent Abstract 62348T-BC, of Japanese Pat. No. 4717781 Sep. 9, 1972.
Ahmed et al., "Purines, Pyrimidines, and Imidazoles, Part XLIV, Syntheses of Some Dihydro-1,3-oxazine Derivatives and Related Substituted Uracils," J.C.S. Perkin I, pp. 1969–1975 (1976).
Yogo et al., "Pyrimidine Derivatives and Related Compounds, 38 (1), Synthesis of 1,3-Oxazine-2,4-diones and Their Reaction with Nucleophiles, Ring Transformation of 1,3-Oxazines to Pyrimidines," J. Heterocyclic Chem. 18, pp. 1095–1100 (Oct., 1981).
Glenn et al., Life Sciences 5: 619 (1966).
C. A. Winter, E. A. Risley, G. W. Nuss, Proc. Soc. Exp. Biol. Med. 111, 544 (1962).
Finney, D. J. (1964) Statistical Method in Biological Assay, Hafner, N.Y.
Boissona, Adv. Org. Chem. 3, 159 (1963).
Windholz et al., Tetrahydron Lett., 8, 2555 (1967).

Primary Examiner—Robert T. Bond
Attorney, Agent, or Firm—Joan Thierstein

[57] ABSTRACT

This invention relates to the use of 6-aryluracils as antiinflammatory and antiarthritic agents and also to both novel intermediates and novel processes for the preparation of selected 6-aryluracils.

6 Claims, No Drawings

6-ARYLURACILS

BACKGROUND OF THE INVENTION

The preparation and use of 6-aryluracils is known. For example, the following references are known: Johnson et al., "Researches on Pyrimidines LXXIV. Synthesis of 4-Phenylcytosine," *J. Amer. Chem. Soc.*, Vol. 37, pp. 378–383 (1915); Gershon et al. "Pyrimidines. III. Some 6-Substituted Di- and Trichloropyrimidines," *J. Med. Chem.*, vol. 6, pp. 87–89 (Jan., 1963); Moszew et al., "New Type of Addition of Aromatic Isocyanates to Benzoylacetamide. 1,6-Diaryl Derivatives of Uracil," *Zesz. Nauk. Univ. Jagiellon.*, Pr. Chem. 1969, No. 14, pp. 31–45, C.A. 72:12242e; and Lacey, "Derivatives of Acetoacetic Acid. Parts V and VI.", *J. Chem. Soc.*, pp. 839–849 (1954). Of these references Gershon et al. and Lacey disclose only anticancer use for related compounds.

Clark et al., "Heterocyclic Studies. Part XIX. Some 6-(Substituted phenyl)-uracil and -thiouracil Derivatives," *J. Chem. Soc. (C).*, pp. 1945–1948 (1971) and Clark et al., "Heterocyclic Studies. Part XXVII. Mass Spectra of 6-(meta- and para- Substituted -phenyl)-uracil and -thiouracil Derivatives", *J. Chem. Soc.*, Perkin II, pp. 233–237 (1972) both teach treatment of hyperthyroidism. Specifically, Clark et al., (1972) discloses that 6-phenyluracil and its p-nitrophenyl analog are thymidine phorphorylase enzyme inhibitors.

Additionally, U.S. Pat. No. 4,171,429 discloses only antiviral and antileukemic activity for various uracils including uracils having 6-aryl substituents. A wide variety of 6-aryl uracils are disclosed in German Offenlegungsschrift Patent No. 2,142,317 but the only utilities taught for the named compounds are as hypnotic and narcotic agents.

Corresponding dihydrouracils are prepared by reduction of N-blocked uracils in a reaction analogous to that disclosed by Hannon et al., *Tetrahedron Letters*, 21, 1105 (1980).

On the other hand, analgetic, antipyretic and antiinflammatory effects are taught for 1,3-disubstituted 6-methyluracils by Senda et al., "Pyrimidine Derivatives and Related Compounds. 15. Synthesis and Analgetic and Antiinflammatory Activities of 1,3-Substituted 5-Amino-6-Methyluracil Derivatives." *J. Med. Chem.*, vol. 15, No. 5, pp. 471–476 (1972).

Ahmed et al. "Purines, Pyrimidines, and Imidazoles. Part XLIV. Synthesis of Some Dihydro-1,3-oxazine Derivatives and Related Substituted Uracils," *J.C.S.* Perkin I, pp. 1969–1975 (1976) discloses a 2-imino-6-methyl-1,3-oxazine derivative analogous to compounds denoted as III herein, but does not teach the novel 6-substituted intermediates II defined hereinafter as the present invention. Ahmed et al. processes for preparing uracils are limited to reactions of beta-keto esters with N,N-dialkyl urea, thus failing to teach the use of the acid addition salt of S-alkylisothiourea VI which provided the unexpected invention process shown hereinafter. In fact, contrary to the present invention Ahmed et al. reiterates the teaching of Lacey that a beta-keto ester can not replace diketene in a reaction with various urea derivatives to produce aryl derivatives of 1,3-oxazine. The alternatives suggested by Ahmed et al. do not alter Lacey's teaching. In other words, the novel intermediates of the present invention are not made obvious by the references.

Finally, Japanese patent application No. J5 7035-515 by Sankyo (denoted hereafter as I) discloses an oxazine derivative having the formula VII teaching immunoregulatory, fungicidal or analgesic activity. Further J4 7017781 also by Sankyo (denoted hereafter as II) having as an abstract Derwent 62348T-BC discloses a preparation of the oxazine derivative by a process which is not related to the chemical process of the present case. In fact, the compund of formula III can not be prepared by the method taught in Sankyo II. Therefore, Sankyo I and II cannot be said to teach the present invention since neither reference discloses a process which can be used to make the present novel intermediate, nor teaches that 6-aryluracils of the present invention are antiarthritic or antiinflammatory agents.

Thus, none of the above references teach the present novel processes or their novel intermediates for preparing selected 6-aryluracils. Further, the unexpected activity for either antiinflammatory or antiarthritic use of the 6-aryluracils as now taught by the present invention is not taught by the noted references.

Belgian Pat. No. 882,315 discloses the preparation and various uses of 6-aryl pyrimidinones including interferon induction, antiviral and immunoregulatory activity. Further, copending U.S. application Ser. No. 303,694 teaches antiarthritic activity for selected compounds within the scope of the Belgian patent.

However, again uses for 6-aryluracils novel intermediates and processes for making selected 6-aryluracils using the novel intermediates of the present invention are not made obvious by either the Belgian Patent or the U.S. application. Particularly, the mechanism of action for the instant use of 6-aryluracils is not understood. For example, 6-aryluracils do not produce neutropenia and agranulocytosis which is indicative of immunosuppressant activity. Further, lymphopenia analogous to corticoid activity is not induced by 6-aryluracils. A functional adrenal gland is not required for 6-aryluracils activity indicating the activity is not dependent on corticosteriod production. Finally, the present 6-aryluracils are clearly different from the related 2-amino-6-arylpyrimidinones of the above noted U.S. application Ser. No. 303,694 because uracils do not induce interferon.

BRIEF SUMMARY OF THE INVENTION

This invention relates to the use of 6-aryluracils as antiinflammatory and antiarthritic agents and also to both novel intermediates and novel processes for the preparation of selected 6-aryluracils.

DETAILED DESCRIPTION OF THE INVENTION

The present invention is for novel intermediates of formula III wherein $R_5$ is hydrogen or bromine;

wherein $R_6$ is $III_6$;

wherein n is a number of from 0 to 3, inclusive; and X is hydroxy, alkyl of from 1 to 8 carbon atoms, inclusive; alkoxy of from 1 to 5 carbon atoms, inclusive; alkylthio of from 1 to 5 carbon atoms, inclusive; halogen; $-NX_1X_2$; aminoalkyl of from 1 to 3 carbon atoms, inclusive; nitro; benzyl; aryl; furyl; pyridyl; or thiophene, and wherein $X_1$ and $X_2$ are the same or different and are alkyl of from 1 to 8 carbon atoms, inclusive; or taken together with $-N$ are a saturated cycloalkylamino group having the formula $X_3$; wherein n' is 3, 4, 5 or 6 or dialkyl substituted cycloalkylamino, wherein each alkyl is from 1 to 3 carbon atoms, inclusive.

Further, the present invention is also a process for the preparation of the compound having formula III (shown as Scheme A)
wherein $R_5$ and $R_6$ are as defined above;
which comprises a process selected from
  step (a) contacting an acid salt of alkylthiopseudourea having formula VI (hereinafter referred to as a compound having formula VI)
  wherein $R_7$ is alkyl of from 1 to 3 carbon atoms, inclusive; with a compound having the formula V
  wherein $R_6$ is as defined above, and $R_2$ is alkyl of from 1 to 8 carbon atoms, inclusive;
in the presence of a strong base to prepare the compound III wherein $R_5$ is hydrogen;
or
  step (a) contacting an acid salt of alkylthiopseudourea having formula Vi
  wherein $R_7$ is alkyl of from 1 to 3 carbon atoms, inclusive; with a compound having the formula V
  wherein $R_6$ is as defined above, and $R_2$ is alkyl of from 1 to 8 carbon atoms, inclusive; in the presence of a strong base; and
  step (b) contacting the product of step (a) with bromine to prepare the compound III wherein $R_5$ is bromine and $R_6$ is as defined above.

Additionally, a total process of the instant invention is for the preparation of a compound having formula $I_1$ (shown as Scheme B);
  wherein $R_5$ and $R_6$ are as defined above, and
  wherein $R_1$ is
  (a) hydrogen;
  (b) alkyl of from 1 to 4 carbon atoms, inclusive or
  (c) benzyl;
with the proviso that if $R_1$ is alkyl it is only a straight chain; which comprises
  step (1) a process selected from
    step (x) contacting an acid salt of alkylthiopseudourea of formula VI
    wherein $R_7$ is as defined above; with a compound having the formula V
    wherein $R_6$ and $R_2$ are as defined above; in the presence of a strong base to prepare a compound III wherein $R_5$ is hydrogen;
  or
    step (x) contacting a compound of formula VI wherein $R_7$ is as defined above with a compound having the formula V
    wherein $R_6$ and $R_2$ are as defined above;
in the presence of a strong base, and
    step (y) contacting the product of step (x) with bromine to prepare compound III wherein $R_5$ is bromine;
and
  step (2) hydrolyzing the compound III of step (1) and
  step (3) contacting the product of step (2) with a compound having the formula $R_1NH_2$ wherein $R_1$ is as defined above to obtain a compound having the formula $I_1$.

Finally, the invention is a process to prepare the compounds $I_2$, $I_3$ or $I_4$ (see Scheme C) wherein $R_1$ is lower alkyl or benzyl with the proviso that if $R_1$ is alkyl it is only a straight chain, and $R_5$ and $R_6$ are hydrogen or bromine with the proviso that $R_5$ is only hydrogen in the compounds $I_3$ or $I_4$ and with the further proviso that $R_6$ does not include nitro; furyl; or thiophene in the compounds $I_3$ or $I_4$ which comprises
  step (1) obtaining the compound $I_1$.
  step (m) alkylating the compound $I_1$ above to obtain $I_2$;
or
  step (n) hydrogenating the compound $I_1$ above to obtain $I_3$;
  step (o) alkylating the compound prepared in step (n) to obtain $I_4$
or
  step (p) hydrogenating the compound of step (m) to obtain $I_4$.

Such hydrogenation and alkylation are carried out by methods analogous to those known in the art described herein.

Finally, the invention contemplates a method for preventing or treating arthritis or for use as an antiinflammatory agent comprising the administration of an effective amount of a compound having the formula I
  wherein $R_1$ is as defined above;
  $R_3$ is hydrogen, alkyl of from 1 to 4 carbon atoms, inclusive, or benzyl;
  Q is $Q_1$ or $Q_2$; and
  $R_5$ is hydrogen or halogen with the proviso that $R_5$ is only hydrogen when Q is $Q_2$;
  $R_6$ is as defined above; or a salt thereof in association with a pharmaceutical carrier to an animal, including man.

The novel intermediates having formula III are understood to exist in several tautomeric forms which may be shown as III⇌III$_1$⇌III$_2$.

Lower alkyl means alkyl of from 1 to 4 carbon atoms, inclusive.

Further, alkyl means methyl; ethyl; propyl; butyl; pentyl; hexyl; heptyl or octyl and isomeric forms thereof but corresponding to the number of carbon atoms noted in each instance or limited if so provided in a proviso; for example, in the $R_1$ position above to only straight chain alkyls.

Halogen means fluoro, chloro, bromo or iodo.

Aryl is phenyl unsubstituted or substituted with, for example, one or more halogen atoms; nitro; aminoalkyl wherein alkyl is from 1 to 3 carbon atoms, inclusive; —$NX_1X_2$ wherein $X_1$ and $X_2$ are as defined above; one or two alkyl groups of from 1 to 3 carbon atoms, inclusive; alkoxy wherein the alkyl is from 1 to 3 carbon atoms, inclusive; alkylthio; benzyl; phenyl; furyl; pyridyl, thiophene; naphthyl unsubstituted or substituted as for phenyl described heretofore up to but not including naphthyl.

A salt of the compound; such as defined for compounds of the formula I or VI, is a suitable pharmaceutically acceptable acid addition salt such as hydrochloride, sulfate, phosphate, nitrate, and the like. These salts can be used in the same manner as the base compounds.

The compounds of the invention and the process for the preparation thereof which are preferred include the compounds having formula III wherein $R_6$ is phenyl. The compounds which are preferred in the process for preventing or treating arthritis or for use as an antiinflammatory agent are the compounds having the formula I wherein $R_1$ is methyl, $R_3$ is hydrogen, Q is $Q_1$ wherein $R_5$ is bromine, and $R_6$ is phenyl; the formula I wherein $R_1$ is methyl, $R_3$ is hydrogen, and Q is $Q_1$ wherein $R_5$ is iodo, and $R_6$ is phenyl; the formula I wherein $R_1$ is methyl, $R_3$ is hydrogen, and Q is $Q_1$ wherein $R_5$ is hydrogen, and $R_6$ is phenyl; and the formula I wherein $R_1$ is methyl, $R_3$ is methyl, and Q is $Q_1$ wherein $R_5$ is bromo, and $R_6$ is phenyl.

Generally, a novel compound having formula II is prepared by reacting an acid salt of alkylthiopseudourea having formula VI with a beta keto ester of formula V in a strong base such as sodium hydroxide or potassium hydroxide; preferably potassium hydroxide, at from 18° C. to 22° C. preferably at about room temperature for from 6 hours to 48 hours, preferably 18 to 24 hours. A compound having formula III wherein $R_5$ is H is obtained. The acid salt of alkylthiopseudourea (VI) is readily available or can be prepared by methods well known in the art. Similarly, the beta keto ester is readily available or can be prepared by methods available in the art such as disclosed in Belgian Pat. No. 882,315 noted above. A by-product, which may be formed in the present process in which compound III is obtained, is a compound having the formula IV wherein $R_5$ and $R_6$ are as defined herein. The compound IV can easily be separated from compound III via an ethanol trituration.

Further, in the process of the invention (preparing the novel compound II), generally, the corresponding compound III of the above reaction is hydrolyzed; for example, with 10 percent hydrogen chloride, and using conditions analogous to a procedure disclosed by Ahmed et al. (cited above) for 6-methyluracils. Quantitative yields of the novel compound having formula II are obtained.

It is necessary to remove the by-product IV if it is formed from the reaction mixture containing compound III wherein $R_5$ is hydrogen prior to hydrolysis since hydrolysis of IV yields a 6 substituted-2,4-pyrimidinedione which cannot easily be separated from the desired product $I_1$ wherein $R_5$ is hydrogen. Longer reaction times increase the probability of the by-product IV formation.

According to the process of the present invention the compound II may then be contacted with a compound of formula $R_1NH_2$ in a manner analogous to that taught on page 1098 of Yogo et al., "Pyrimidine Derivatives and Related Compounds. 38 (1). Synthesis of 1,3-Oxazine-2,4-diones and Their Reaction With Nucleophiles. Ring Transformation of 1,3-Oxazines to Pyrimidines," *J. Hetercyclic Chem.*, 18, pp. 1095–1100 (October, 1981).

In the alternative an additional step; which for convenience is denoted step (1b) as shown in Scheme A and step (1y) in Scheme B, the compound III wherein $R_5$ is hydrogen may generally be contacted with bromine or a bromine bearing compound; for example $Br_2$, or the like in the presence of a strong base at a temperature of preferably at about 50° C. This bromination of compound III may be accomplished in a manner analogous to the bromination of pyrimidinones disclosed in Belgium Pat. No. 882,315.

In the process of the invention to prepare compound $I_1$ wherein $R_5$ is bromine, generally, the corresponding compound III of the step 1b) described above may be treated; in a one pot reaction, with the $R_1NH_2$ and hydrolyzing agent. The preparation of compound $I_1$ wherein $R_5$ is bromine may also be shown as steps 2–3 in Scheme B. Conditions of steps 2–3 are again analogous to those recited for step (2) and step (3) above. However, although the conditions are analogous the steps are performed without separation of an intermediate from the (2) and (3) reaction mixture.

For either step (2) or step (3) and for steps 2–3 as shown in Scheme B, variations in reaction conditions of Ahmed et al. and Yogo et al. respectively may be appropriate for the present invention and would be evident to the ordinarily skilled artisan.

A process for the alkylation at the 3-N position of the compound of formula $I_1$ wherein $R_3$ is hydrogen or of formula $I_3$ is readily apparent to one of ordinary skill in the art. See Scheme C.

The methods of the present invention relate to the treatment of animals preferably mammals and most preferably humans. The present invention thus provides a method of treating both humans and valuable domestic animals such as bovine, equine, canine, and feline species, and chickens, turkeys, geese, ducks, and other fowl.

The present invention relates to the arrest or prophylaxis of an arthritic or inflammatory condition by the administration of a compound having the formula I wherein $R_1$, $R_3$ and Q are all as previously defined. The employment of sound medical therapy requires that administration be employed prophylactically only in cases where the animal or patient is particularly susceptible to the development of arthritic or inflammatory conditions. The conditions are circumstances which increase susceptibility are readily ascertained to the ordinarily skilled physician or veterinarian.

In the prophylactic use of a compound having the formula I, the dose effective for the prevention of arthritis or inflammation is determined by patient or animal response, as discussed hereinafter for therapeutic uses, and is, in general, somewhat less than the dose required to treat an arthritic or inflammatory condition.

Arthritis or inflammation which is arrested or prevented in accordance with the present invention is not an uncommon condition encountered in medical or veterinary practice and includes the condition or state associated with a direct or indirect pathological process which is readily diagnosed by the ordinarily skilled physician or veternarian.

Systemic routes of administration for compounds of the present invention are known. See Offenlegenschrift Pat. No. 2,142,317. In the present invention the most preferred route of administration is by oral method. Other systemic routes of administration may be appropriate, such as intraarticular. Alternate or concurrent administration by more than one route of administration may be used. A pharmaceutically acceptable form prepared by methods known in the pharmaceutical arts for various routes of administration are obvious. Powders, pastes, liquids, gels, viscous fluids or compressed tablets are among the various forms well known in the art.

Many different methods have been and are used to evaluate antiarthritic or antiinflammatory activity. Different tests may be used to determine whether or not a new compound is antiarthritic or antiinflammatory or not, therefore, evidence by one or more of the various tests establishes the presence of antiarthritic or antiinflammatory action of the present invention. Antiarthritic or antiinflammatory activity of the compounds of formula I and their pharmacologically acceptable acid addition salts are found in one or more of the following tests:

INHIBITION OF ADJUVANT-INDUCED ARTHRITIS

Charles River male rats, 200–225 grams in weight, are injected subcutaneously in the tail with 0.4 mg adjuvant (*Mycobacterium butyricum* in mineral oil) on day 0. Drug treatment is initiated on the same day and continued for a total of 15 to 16 days or according to an intermittent treatment regimen. Drugs are given orally in water in a volume of 1.0 ml/rat. Groups of 5 to 10 animals are used for each dose level. Control rats are injected with adjuvant and treated with vehicle. Following the treatment period, visual severity of arthritis is recorded for each paw of each animal; a numerical value of 4 for each appendage equals maximum arthritis. (The maximum score possible for each animal is 16, if maximum arthritis is noted in all four paws). The incidence of arthritis in these animals is also recorded. Final expression is by percent inhibition of treated compared to control.

Sixteen hours after the last dose of drug, rats are anesthetized with the sodium salt of 5-ally-1-5-(2-cyclopentene-1-yl) barbituric acid (5.0 ml/kg of a 1 percent solution, I.P.). Rats are exsanquinated from the dorsal aorta with heparinized syringes. In some cases, plasmas are obtained from rats by inserting heparinized capillary tubes into the orbital sinuses. This procedure elicits no pain and discomfort in the experimental animals.

PLASMA INFLAMMATION UNITS

Inflammation units are determined by diluting plasmas 1:200 in sterile physiological saline. The initial turbidity of the diluted solutions is determined in a Coleman #9 Nephelometer, set at full sensitivity, against a saline blank. Duplicate samples and blanks are heated subsequently in a water bath at 56° C. for 30 minutes. They are cooled to room temperature. The increase in turbidity is determined again with the Nephelometer. The differences between initial and final Nephelometric readings are expressed as inflammation units. These units may have an uncertain relationship to fibrinogen. Starch-gel electrophoresis of plasmas show the heat-precipitate protein to consist of fibrinogen, alpha globulins, beta globulins and albumen. For descriptive purposes only, precipitable protein fractions are called "inflammation units." This designation describes accurately the biologic stimulus (inflammation) which increases this component in the plasma.

This procedure is described by Glenn et al., *Life Sciences* 5: 619 (1966).

REVERSED PASSIVE ARTHUS REACTION (RPAR)

Male, Wistar rats (Charles River, Wilmington, MA), 175-200 grams, are anesthetized with ether and injected in the penile vein with 1 mg bovine serum albumin (BSA; Sigma Chemical Co., St. Louis, MO.) in 0.2 ml saline. The rats are individually numbered by ear punch with 5 rats constituting a control or treatment group. Sixty minutes following sensitization each rat is given a subplantar injection of 100-200 μg rabbit anti-bovine albumin (anti-BSA; 1gG Fraction; Cappel Laboratories, Cochranville, PA) in 0.2 ml saline. The subcutaneous injection is given toward the toes of the left hind paw in order to localize the antibody (AB) and the subsequent RPAR. Immediately following the hindpaw injection, the injected paw of each rat is weighed by mercury displacement in a plethysmograph ("0 Time") with the displaced weight of Hg recorded on a Texas Instrument ASR 733 printer-cassette cassette tape recorder. Paws are immersed in Hg up to the walking pad closest to the body.

Plethysmograph readings are taken 2 hours post-challenge from which "0 Time" measurements of individual rats are subtracted to give 2 hour differences for each rat. Mean differences of treatment groups were used to calculate percent inhibition of paw swelling as compared to controls.

INHIBITION OF CARRAGEENAN-INDUCED EDEMA

This procedure determines antiinflammatory activity as reflected by inhibition of carrageenan-induced edema in rats [(method of C. A. Winter, E. A. Risley, G. W. Nuss, *Proc. Soc. Exp. Biol. Med.* 111, 544 (1966)].

Groups of 10 male Sprague-Dawley rats weighing 180-220 grams after overnight fasting are dosed orally with either the test agent or the vehicle. One hour later, the right hind paw of each animal is injected with 0.1 ml or 0.5 ml of 0.5 percent carrageenan. The left hind paw serves as a control for each animal. Three hours after carrageenan injection, both paws are amputated and weighted. The difference in paw weights indicates the amount of fluid produced. Comparison of fluid produced in the treated group with that of the control group reveals the inhibition of edema. Active compounds are tested further using expanded dose levels and their potency relative to a standard agent, such as aspirin or ibuprofen, determined either graphically or statistically (parallel line assay described in Finney, D. J., 1964, *Statistical Method in Biological Assay*, Hafner, N.Y.).

After the onset of arthritis or inflammation has been diagnosed by the attending physican or veterinarian, the treatment with the compounds having formula I in accordance with the present invention may be initated promptly. Results of animal studies show the compounds having formula I have an $ED_{50}$ of approximately 100 to 200 mg/kg per oral dose per day and a projected $LD_{50}$ of 400 to 600 mg/kg/day. For convenience, dosages may be administered at periodic intervals throughout the day.

When initial dosages at the lower end of the range are employed, the mammals progress is monitored and dosages on subsequent days are increased in the event that the response is deemed by the attending physician or veterinarian to be absent or insufficient. At the same time, the systemic toxicity of the compounds having formula I must be carefully monitored to evaluate the benefits of the drug in relationship to any such toxic manifestations.

The various compounds having the formula I are all employed in any conventional, pharmaceutically acceptable form. Thus, these agents are optionally employed as free bases, or salts.

A compound having the formula I can be prepared by methods disclosed in the references discussed above, by methods known in the art, or by methods within the skill of the ordinary artisan.

The compounds having the formula $I_3$ may be prepared by reduction of nitrogen blocked compounds of formula $I_1$ wherein $R_5$ uracils is in a manner analogous to that described by Hannon et al., *Tetrahedron Letters*, 21, 1105 (1980). In like manner, compounds having the formula $I_4$ may be prepared from compounds of formula $I_2$. See Scheme C.

For a compound having the formula I wherein Q is $Q_2$ analogous hydrogenation of a compound having the formula I wherein Q is $Q_1$ wherein $R_5$ is hydrogen may be used.

Blocking groups of the nitrogen blocked compounds referred to above are sometimes called "protective groups" in the art and are well known in many fields of organic chemistry, including peptide chemistry, fatty acid chemistry and especially semi-synthetic and synthetic antibiotic chemistry. Two commonly used blocking groups are carbobenzyloxy and t-butoxycarbonyl. Such groups can be removed easily and replaced by hydrogen atoms with suitable treatments, which may vary in detail depending on the particular blocking group and the particular molecule to which it is bonded, with acids or by reduction. Regarding the chemistry of adding and removing such blocking groups, see, e.g., Boissona, Adv. Org. Chem. 3, 159 (1963) and Windholz et al., *Tetrahedron Lett.*, 8, 2555 (1967).

The hydrogenation conditions required in the above noted reduction of nitrogen blocked compounds may vary with the a compound having the formula I being hydrogenated but such variations are within the skill in the art.

The following preparations and examples describe the preparation of the novel compounds III and the novel processes of the invention. These preparations and examples are indicative of the scope of this invention but are not to be construed to be limitative. Those skilled in the art will recognize appropriate variations from the processes both as to precursors as well as reaction conditions and techniques. Starting materials used in the process of this invention can be prepared by known methods, are known; for example, as noted above, and/or are available commercially. These preparations and examples indicate the best mode presently known to the inventor.

PREPARATION Ia

2-Amino-6-Phenyl-1,3-Oxazine-4-One (Scheme A step a)

To 9.45 g (0.034 M) of methylthiopseudourea $H_2SO_4$ is added 40.0 ml of $H_2O + 8.0$ g (0.142 M) of KOH. With vigorous stirring, 12.0 g (0.0625 M) of ethyl benzoylacetate (Aldrich) is also added and the heterogenous mixture allowed to stir at ambient temperature for 18 hours. The resulting solids are filtered and washed very well with $H_2O$ followed by ether. The solids are dried at 60° C. in a vacuum oven to yield 7.20 g (61.3 percent) of 2-amino-6-phenyl-1,3-oxazine-4-one. An analytical sample is recrystallized from 95 percent EtOH:DMF to yield 2-amino-6-phenyl-1,3-oxazine-4-one (m.p. 244–246 d).

Calculated for $C_{10}H_8N_2O$: C, 63.82; H, 4.28; N, 14.89. Found: C, 63.45; H, 4.45; N, 15.02.

Mass spec. calculated 188.0568, found 188.0586.

$H^1$ NMR ($d_6DMSO$): 8.08–7.81 (m, 2H, $\phi H$); 7.71–7/50 (m, 3H, $\phi H$); 6.53 (s, 1H, vinyl).

Utilizing a procedure similar to the Preparation Ia above but substituting the appropriate ethyl acetate, there is obtained the corresponding 2-amino-6-aryl-1,3-oxazine-4-one as follows:

1. 2-amino-6-p-hydroxyphenyl-1,3-oxazine-4-one;
2. 2-amino-6-p-hexylphenyl-1,3-oxazine-4-one;
3. 2-amino-6-m-methylphenyl-1,3-oxazine-4-one;
4. 2-amino-6-o-propylphenyl-1,3-oxazine-4-one;
5. 2-amino-6-o-methoxyphenyl-1,3-oxazine-4-one;
6. 2-amino-6-p-ethylthioxyphenyl-1,3-oxazine-4-one;
7. 2-amino-6-o-bromophenyl-1,3-oxazine-4-one;
8. 2-amino-6-p-fluorophenyl-1,3-oxazine-4-one;
9. 2-amino-6m-chlorophenyl-1,3-oxazine-4-one;
10. 2-amino-6-o-fluorophenyl-1,3-oxazine-4-one;
11. 2-amino-6-o-dimethylaminophenyl-1,3-oxazine-4-one;
12. 2-amino-6-p-piperidinylphenyl-1,3-oxazine-4-one;
13. 2-amino-6-m-(4-methylpiperidinyl)phenyl-1,3-oxazine-4-one;
14. 2-amino-6-o-aminopropylphenyl-1,3-oxazine-4-one;
15. 2-amino-6-p-nitrophenyl-1,3-oxazine-4-one;
16. 2-amino-6-m-benzylphenyl-1,3-oxazine-4-one;
17. 2-amino-6-o-phenylphenyl-1,3-oxazine-4-one;
18. 2-amino-6-p-(4-fluorophenyl)phenyl-1,3-oxazine-4-one;
19. 2-amino-6-m-(3-methylphenyl)phenyl-1,3-oxazine-4-one;
20. 2-amino-6-o-(2-dimethylaminophenyl)phenyl-1,3-oxazine-4-one;
21. 2-amino-6-p-naphthylphenyl-1,3-oxazine-4-one;
22. 2-amino-6-m-furylphenyl-1,3-oxazine-4-one;
23. 2-amino-6-o-pyridylphenyl-1,3-oxazine-4-one;
24. 2-amino-6-p-thienylphenyl-1,3-oxazine-4-one;
25. 2-amino-6-(2,4-dihydroxyphenyl)-1,3-oxazine-4-one;
26. 2-amino-6-(3,5-diethylphenyl)-1,3-oxazine-4-one;
27. 2-amino-6(2,3-dimethoxyphenyl)-1,3-oxazine-4-one;
28. 2-amino-6-(3,4-dipropylthioxyphenyl)-1,3-oxazine-4-one;
29. 2-amino-6-(2,6-difluorophenyl)-1,3-oxazine-4-one;
30. 2-amino-6-(3,5-methylithylaminophenyl)-1,3-oxazine-4-one;
31. 2-amino-6-(2,4-diaminomethylphenyl)-1,3-oxazine-4-one;
32. 2-amino-6-(3,5-dinitrophenyl)-1,3-oxazine-4-one;
33. 2-amino-6-(3,5-dibenzylphenyl)-1,3-oxazine-4-one;
34. 2-amino-6-(3,4-diphenylphenyl)-1,3-oxazine-4-one;
35. 2-amino-6-(2,6-difurylphenyl)-1,3-oxazine-4-one;
36. 2-amino-6-(2,3-dipyridylphenyl)-1,3-oxazine-4-one;
37. 2-amino-6-(2,4-dithienylphenyl)-1,3-oxazine-4-one;
38. 2-amino-6-(2,4,6-trihydroxyphenyl)-1,3-oxazine-4-one;
39. 2-amino-6-(3-ethyl-5-methyl-6-propylphenyl)-1,3-oxazine-4-one;
40. 2-amino-6-(2,3,4-trimethylthioxyphenyl)-1,3-oxazine-4-one;
41. 2-amino-6-(2,4,6-trifluorophenyl)-1,3-oxazine-4-one;
42. 2-amino-6-(3,5,6-trimethylethylaminophenyl)-1,3-oxazine-4-one;
43. 2-amino-6-(2,3,4-triaminomethylphenyl)-1,3-oxazine-4-one;
44. 2-amino-6-(2,4,6-trinitrophenyl)-1,3-oxazine-4-one;
45. 2-amino-6-(3,5,6-tribenzylphenyl)-1,3-oxazine-4-one;
46. 2-amino-6-(2,3,4-tri-p-fluorophenyl)-1,3-oxazine-4one;
47. 2-amino-6-(2,4,6-trifurylphenyl)-1,3-oxazine-4-one;
48. 2-amino-6-(3,5,6-tripyridylphenyl)-1,3-oxazine-4-one;
49. 2-amino-6-(2,4,5-trithienylphenyl)-1,3-oxazine-4-one;

PREPARATION Ib

2-Amino-5-Bromo-6-Phenyl-1,3-Oxazine-4-One (Scheme A steps a and b)

To 1.88 g (10 mM) of 2-amino-6-phenyl-1,3-oxazine-4-one from Preparation Ia is added 11.0 ml of a 1 N NaOH solution and 100 ml of $H_2O$. The mixture is heated to reflux to dissolve all the solids, cooled to 50° C. and with stirring, a solution of 550 μl of $Br_2$ in 100 ml of $CHCl_3$ is added, then sufficient 1 N NaOH is added to keep the aqueous mixture neutral, and stirring is continued at ambient temperature for 24 hours. The resulting solids are filtered, washed well with $H_2O$ and dried to yield 215 mg of 2-amino-6-phenyl-1,3-oxazine-4-one.

The supernatant is evaporated to dryness and chromatographed over 50 g silica gel using 1.2 acetone:cyclohexane as eluent to yield pure 2-amino-5-bromo-6-phenyl-1,3-oxazine-4-one, r.f. 0.35 in 1:1 acetone:cyclohexane, 0.4 in 10 percent MeOH:CHCl$_3$.

Calculated for $C_{10}H_7BrN_2O_2$: C, 44.96; H, 2.65; N, 10.49. Found: C, 45.23; H, 2.70; N, 10.46.

Utilizing a procedure similar to the Preparation Ib noted above but substituting the appropriate ethyl arylacetate, there is obtained the corresponding 2-amino-5-bromo-6-aryl-1,3-oxazine-4-one as follows:

1. 2-amino-6-p-hydroxyphenyl-1,3-oxazine-4-one;
2. 2-amino-6-p-hexyphenyl-1,3-oxazine-4-one;
3. 2-amino-6-m-methylphenyl-1,3-oxazine-4-one;
4. 2-amino-5-bromo-6-o-propylphenyl-1,3-oxazine-4-one;
5. 2-amino-6-o-methoxyphenyl-1,3-oxazine-4-one;
6. 2-amino-6-p-ethylthioxyphenyl-1,3-oxazine-4-one;
7. 2-amino-6-o-bromophenyl-1,3-oxazine-4-one;
8. 2-amino-5-bromo-6-p-fluorophenyl-1,3-oxazine-4-one;
9. 2-amino-6-m-chlorophenyl-1,3-oxazine-4-one;
10. 2-amino-6-o-fluorophenyl-1,3-oxazine-4-one;
11. 2-amino-6-o-dimethylaminophenyl-1,3-oxazine-4-one;
12. 2-amino-5-bromo-6-p-piperidinylphenyl-1,3-oxazine-4-one;
13. 2-amino-6-m-(4-methylpiperidinyl)phenyl-1,3-oxazine-4-one;
14. 2-amino-6-o-aminopropylphenyl-1,3-oxazine-4-one;
15. 2-amino-6-p-nitrophenyl-1,3-oxazine-4-one;
16. 2-amino-5-bromo-6-m-benzylphenyl-1,3-oxazine-4-one;
17. 2-amino-6-o-phenylphenyl-1,3-oxazine-4-one;
18. 2-amino-6-p-(4-fluorophenyl)phenyl-1,3-oxazine-4-one;
19. 2-amino-6-m-(3-methylphenyl)phenyl-1,3-oxazine-4-one;
20. 2-amino-5-bromo-6-o-(2-dimethylaminophenyl)phenyl-1,3-oxazine-4-one;
21. 2-amino-6-p-naphthylphenyl-1,3-oxazine-4-one;
22. 2-amino-6-m-furylphenyl-1,3-oxazine-4-one;
23. 2-amino-6-o-pyridylphenyl-1,3-oxazine-4-one;
24. 2-amino-5-bromo-6-p-thienylphenyl-1,3-oxazine-4-one;
25. 2-amino-6-(2,4-dihydroxyphenyl)-1,3-oxazine-4-one;
26. 2-amino-6-(3,5-diethylphenyl)-1,3-oxazine-4-one;
27. 2-amino-6-(2,3-dimethoxyphenyl)-1,3-oxazine-4-one;
28. 2-amino-5-bromo-6-(3,4-dipropylthioxyphenyl)-1,3-oxazine-4-one;
29. 2-amino-6-(2,6-difluorophenyl)-1,3-oxazine-4-one;
30. 2-amino-6-(3,5-methylithylaminophenyl)-1,3-oxazine-4-one;
31. 2-amino-6-(2,4-diaminomethylphenyl)-1,3-oxazine-4-one;
32. 2-amino-5-bromo-6-(3,5-dinitrophenyl)-1,3-oxazine-4-one;
33. 2-amino-6-(3,5-dibenzylphenyl)-1,3-oxazine-4-one;
34. 2-amino-6-(3,4-diphenylphenyl)-1,3-oxazine-4-one;
35. 2-amino-6-(2,6-difurylphenyl)-1,3-oxazine-4-one;
36. 2-amino-5-bromo-6-(2,3-dipyridylphenyl)-1,3-oxazine-4-one;
37. 2-amino-6-(2,4-dithienylphenyl)-1,3-oxazine-4-one;
38. 2-amino-6-(2,4,6-trihydroxyphenyl)-1,3-oxazine-4-one;
39. 2-amino-6-(3-ethyl-5-methyl-6-propylphenyl)-1,3-oxazine-4-one;
40. 2-amino-5-bromo-6-(2,3,4-trimethylthioxyphenyl)-1,3-oxazine-4-one;
41. 2-amino-6-(2,4,6-trifluorophenyl)-1,3-oxazine-4-one;
42. 2-amino-6-(3,5,6-trimethylethylaminophenyl)-1,3-oxazine-4-one;
43. 2-amino-6-(2,3,4-triaminomethylphenyl)-1,3-oxazine-4-one;
44. 2-amino-5-bromo-6-(2,4,6-trinitrophenyl)-1,3-oxazine-4-one;
45. 2-amino-6-(3,5,6-tribenzylphenyl)-1,3-oxazine-4-one;
46. 2-amino-6-(2,3,4-tri-p-fluorophenyl)-1,3-oxazine-4-one;
47. 2-amino-6-(2,4,6-trifurylphenyl)-1,3-oxazine-4-one;
48. 2-amino-5-bromo-6-(3,5,6-tripyridylphenyl)-1,3-oxazine-4-one;
49. 2-amino-6-(2,4,5-trithienylphenyl)-1,3-oxazine-4-one;

PREPARATION Ia(1)

6-Phenyl-1,3-Oxazine-2,4-Dione (Scheme B step 2)

To 230 mg (1.22 mM) of powdered 2-amino-6-phenyl-3-oxazine-4-one from Preparation Ia is added 8 ml of a 10 percent aqueous HCl solution. The reaction mixture is heated, with stirring, at reflux for 30 minutes. The reaction mixture is allowed to cool to room temperature and filtered, washed the solids well with H$_2$O and dried at 60° C. in vacuum oven for 18 hours. Yield of 6-phenyl-1,3-oxazine-2,4-dione is 230 mg (100 percent), m.p. >210° C. Recrystallization from 95 percent EtOH gives 6-phenyl-1,3-oxazine-2,4-dione.

Calculated for $C_{10}H_7NO_3$: C, 63.49; H, 3.72; N, 7.40. Found: C, 63.41; H, 3.78; N, 7.32.

H -NMR (d$_6$DMSO): 7.95–7.78 (m, 2H, $\phi$H); 7.60–7.43 (m, 3H, $\phi$H); 6.65 (s, 1H, vinyl).

EXAMPLE I

1-N-Methyl-6-Phenyl-2,4Pyrimidine-Dione (Scheme B step 3)

To 189 mg (1 mM) of 6-phenyl-1,3-oxazine-2,4-dione from Preparation Ia(1) is added 10 ml of a 40 percent aqueous CH$_3$NH$_2$ solution. The reaction mixture is allowed to heat at reflux for 18 hours. The resulting solution is cooled to room temperature and the precipitate filtered, washed well with water, and dried at 60° C. under vacuum. The yield is 146 mg (72 percent) (m.p. 183°–185° C.) of 1-N-methyl-6-phenyl-2,4-pyrimidinedione.

Calculated for $C_{11}H_{10}N_2O_2$: C, 65.34; H, 4.98; N, 13.85. Found: C, 65.18; H, 4.98; N, 13.79.

H$^1$-NMR (d$_6$-DMSO): 7.55 (s, $\phi$H); 5.45 (s, 1H, vinyl H); 3.03 (s, 3H, N-CH$_3$).

PREPARATION IIa

2-Amino-6-m-fluorophenyl-1,3-Oxazine-4-One (Scheme A step a)

To 16.6 g (0.597 M) of methylthiopseudourea sulfate is added 66 ml of H$_2$O + 13.0 g of KOH. With vigorous stirring, 20 g (71.9 mM) of ethyl-m-fluorobenzoylacetate is added and the reaction is allowed to stir, at ambient temperature, for 18 hours. The solids are filtered and washed well with H$_2$O followed by diethylether. The crude title compound is dried at 60° C. in a vacuum over to yield 16.0 g (>100 percent). To 6.8 g of crude powdered oxazine is added 100 ml of H$_2$O and heated to 70° C., cooled, filtered and washed solids. Yield of 2-amino-6-m-fluorophenyl-1,3-oxazine-4-one of 3.60 g (53 percent of rec. yield).

Calculated for $C_{10}H_7FN_2O_2$: C, 58.25; H, 3.39; N, 13.59. Found: C, 57.88; H, 3.69; N, 13.15.

H-NMR ($d_6$-DMSO)-7.83–7.22 (M, 3H, $\phi$); 6.61 (s, 1H, vinyl).

PREPARATION IIa(1)

6-m-Fluorophenyl-1,3-Oxazine-2,4-Dione (Scheme B step 2)

To 1.50 g (7.28 mM) of powdered 2-amino-6m-fluorophenyl-1,3-oxazine-4-one from Preparation IIa is added 30 ml of a 10 percent aqueous HCl solution. With vigorous stirring the reaction mixture is heated at reflux for 55 minutes. The reaction mixture is cooled, filtered and the solids washed well with $H_2O$. Drying at 60° C. in a vacuum oven yields 1.25 g (83.3 percent) of crude 6-m-fluoro-1,3-oxazine-2,4-dione. Recrystallization from $CH_3OH:H_2O$ gave 650 mg (m.p. 179–181) of 6-m-fluorophenyl-1,3-oxazine-2,4-dione. An additional 490 mg is recovered from the M's.

Calculated for $C_{10}H_6FNO_3$: C, 57.97; H, 2.91; N, 6.76; F, 9.17. Found: C, 57.83; H, 2.97; N, 6.90; F, 9.54.

$H^1$-NMR ($d_6$DMSO)-7.83–7.61 (M, 3H, $\phi H$); 6.83 (s, 1H, benzyl).

EXAMPLE II

1-N-Methyl-6-M-Fluorophenyl-2,4-Pyrimidine-Dione (Scheme B step 3)

To 490 mg (2.36 mM) of 6-m-fluorophenyl-1,3-oxazine-2,4-dione of Preparation IIa(1) is added 30.0 ml of a 40 percent aq. $CH_3NH_2$ solution. The reaction solution is heated at reflux for 18 hours. The solution is cooled and evaporated to dryness, under vacuum, to yield an amber solid. The solid is dissolved in $CH_3OH$ (hot), treated with darco, filtered and the $CH_3OH$ filtrate is evaporated to a white solid. The solid is recrystallized from $H_2O$ to yield 280 mg (54 percent) (m.p.: 192–194) of 1-N-methyl-6-m-fluorophenyl-2,4-pyrimidine-dione.

Calculated for $C_{11}H_9FN_2O_2$: C, 59.99; H, 4.11; N, 12.72. Found: C, 59.73; H, 4.04; N, 12.78.

$H^1$-NMR ($d_6$-DMSO): 7.75–7.25 (m, 4H, $\phi$); 5.5 (s, 1H, vinyl); 3.05 (s, 3H, N-$CH_3$).

EXAMPLE III 5,6-Dihydro-1-Methyl-6-Phenyl-2,4-Pyrimidine-Dione

A solution of 1-methyl-6-phenyluracil (0.65 g) in dimethylformamidine (15 ml) is treated with 10 percent palladium on carbon and reduced at 40 p.s.i. for 20 hours. The catalyst is then filtered and the filtrate evaporated to a crystalline residue. The crystallization from acetonitrile provides 5,6-dihydro-1-methyl-6-phenyl-2,4-pyrimidine-dione, m.p. 155°–6° C.

Infrared (mull). 860, 920, 940, 1065, 1160, 1215, 1225, 1245, 1270, 1305, 1370, 1410, 1500, 1700, 3045, 3160 cm$^{-1}$.

H NMR (DMSO) $\delta$ 2.83 (S, 3, $CH_3$), 3.55-3.4 (m, 2, $CH_2$), 3.65 (q, 1, CH), 7.1–7.7 (m, 5, ArH).

Mass spec: m/e 204(m+) 127, 120, 118, 104, 84.

Anal. Calcd. for $C_{11}H_{12}N_2O_2$: C, 64.69; H, 5.92 N, 13.72. Found: C, 64.65; H, 5.98; N, 13.42.

EXAMPLE IV 5,6-Dihydro-3-Ethyl-1-Methyl-6-Phenyl-2,4-Pyrimidine-Dione

A solution of 3-ethyl-1-methyl-6-phenyl-2,4-pyrimidinedione (1.0 g) in methanol (50 ml) is treated with magnesium (1.05 g, 43.4 g atoms) and reacted at ambient temperature. After an induction period of 60 minutes, an exothermic reaction begins and is modulated by cooling to 25° C. The reaction proceeds for 60 minutes, the methanol solution is decanted from unreacted magnesium and evaporated. The residue is treated with 1N HCl and the precipitate is extracted into ethylacetate. Drying and evaporation of the solvent gives a product (1.1 g). Purification on silica gel (150 g) using 3:1 Skellysolve B: ethyl acetate as eluent gives pure 5,6-dihydro-3-ethyl-1-methyl-6-phenyl-2,4-pyrimidine-dione.

(0.66 g) as an oil, Rf 0.39 (silica gel tlc, 1:1 ethyl acetate:cyclohexane solvent).

Infrared (film): 960, 990, 1055, 1090, 1140, 1215 (sh), 1240, 1275, 1310, 1350, 1390, 1420, 1440, 1490, 1680, 1715, and 2900–2975 cm$^{-1}$.

H-NMR ($CDCl_3$): 1.13 (t, 3, $CH_3CH_2$), 2.65–3.50 (M, 2, $CH_2$), 3.02 (S, 3, $CH_3$), 3.89 (q, 1, $CH_2$), 6.85–7.6 (m, 5, ArH). Mass Spec.: m/e 232 (M+), 217, 189, 104.

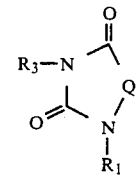

I

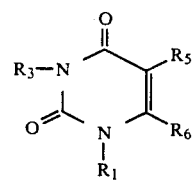

$I_1$

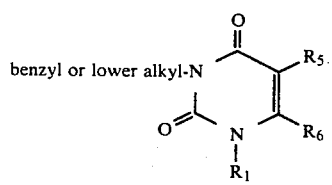

$I_2$

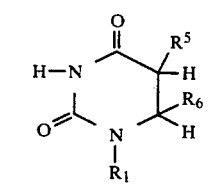

$I_3$

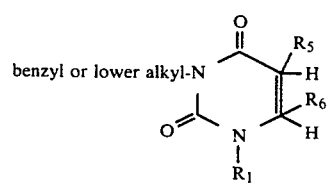

$I_4$

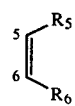

$Q_1$

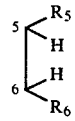

$Q_2$ 4,495,349

15

-continued

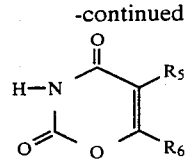
II

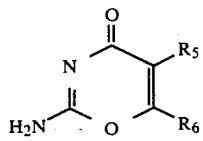
III

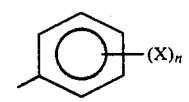
III$_6$

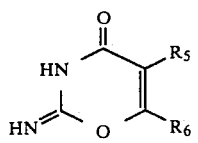
III$_1$

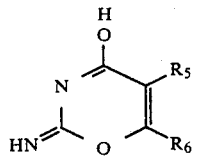
III$_2$

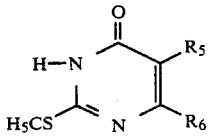
IV

V

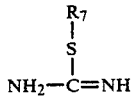
VI

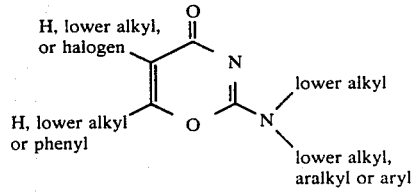
VII

H, lower alkyl, or halogen
H, lower alkyl or phenyl
lower alkyl
lower alkyl, aralkyl or aryl

X$_3$

SCHEME A

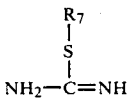
VI

16

-continued
SCHEME A step 1
(a) R$_6$CCH$_2$COR$_2$    V
or
(a) R$_6$CCH$_2$COR$_2$    V
and
(b) brominating agent

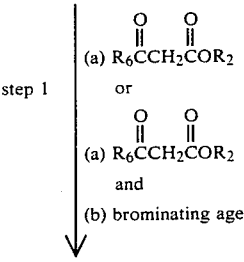
III

SCHEME B

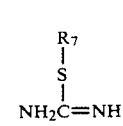
VI step 1
(x) R$_6$CCH$_2$COR$_2$    V
or
(x) R$_6$CCH$_2$COR$_2$    V
and
(y) brominating agent

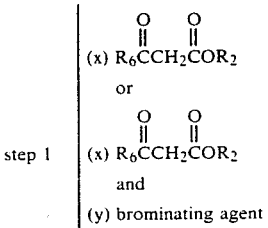
III hydrolysis
step 2 (10 percent HCl)

steps 2-3  R$_1$NH$_2$ and H$^+$

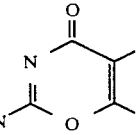
II step 3 | R$_1$NH$_2$

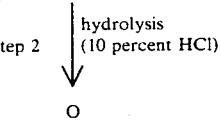
I$_1$

SCHEME C

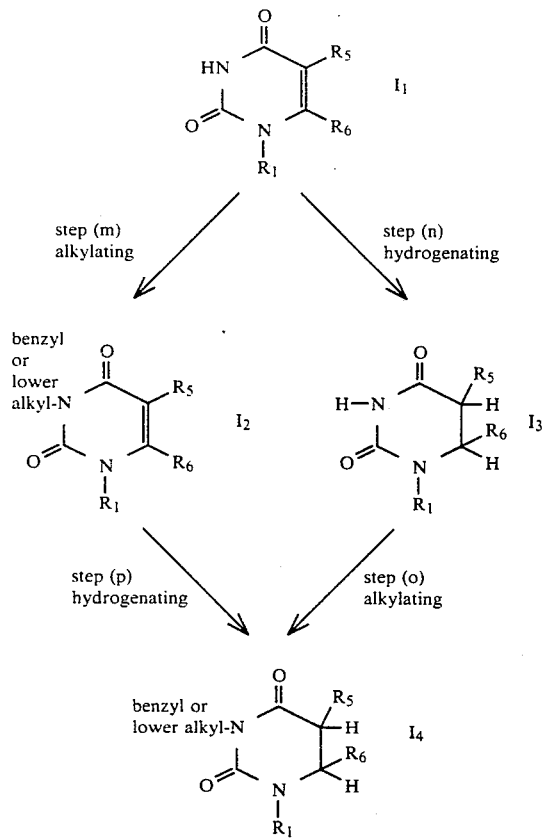

We claim:

1. A compound having the formula

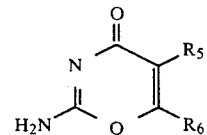

wherein $R_5$ is hydrogen or bromine; and $R_6$ is a member selected from the group consisting of

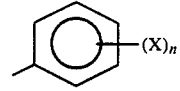

wherein n is a number of from 0 to 3, inclusive; and
X is hydroxy, alkyl of from 1 to 8 carbon atoms, inclusive; alkoxy of from 1 to 5 carbon atoms, inclusive; alkylthio of from 1 to 5 carbon atoms, inclusive; nitro; —$NX_1X_2$; aminoalkyl of from 1 to 3 carbon atoms, inclusive; halogen; benzyl; aryl; furyl; pyridyl; or thiophene, and wherein $X_1$ and $X_2$ are the same or different and are alkyl of from 1 to 8 carbon atoms, inclusive; or taken together with —N are a saturated cycloalkylamino group —N⌒$C_{n'}$; wherein n' is 3, 4, 5 or 6 or dialkyl substituted cycloalkylamino, wherein each alkyl is from 1 to 3 carbon atoms, inclusive and pharmaceutically acceptable salts thereof.

2. A compound according to claim 1 wherein $R_5$ is hydrogen.

3. A compound according to claim 2 wherein $R_5$ is hydrogen and $R_6$ is phenyl so that the preferred embodiment is 2-amino-6-phenyl-1,3-oxazine-4-one.

4. A compound according to claim 2 wherein $R_5$ is hydrogen and $R_6$ is meta-fluoro-phenyl so that the preferred embodiment is 2-amino-6-m-fluorophenyl-1,3-oxazine-4-one.

5. A compound according to claim 1 wherein $R_5$ is bromine.

6. A compound according to claim 5 wherein $R_5$ is bromine and $R_6$ is phenyl so that the preferred embodiment is 2-amino-5-bromo-6-phenyl-1,3-oxazine-4-one.

* * * * *